United States Patent [19]
Ullman et al.

[11] Patent Number: 4,532,203
[45] Date of Patent: Jul. 30, 1985

[54] FLUORESCENT DETERMINATION OF MICROLYMPHOCYTOTOXICITY

[75] Inventors: Edwin F. Ullman, Atherton; F. Carl Grumet, Stanford, both of Calif.

[73] Assignee: SYVA Company, Palo Alto, Calif.

[21] Appl. No.: 436,770

[22] Filed: Oct. 26, 1982

[51] Int. Cl.³ ............................................. G01N 33/54
[52] U.S. Cl. .......................................... 435/7; 435/29; 435/34; 436/501; 436/519; 436/546; 436/548; 436/800; 436/821; 436/824
[58] Field of Search ...................... 435/4, 7, 29, 30, 34; 436/518, 519, 543, 546, 548, 800, 821, 823, 824, 63, 501

[56] References Cited
U.S. PATENT DOCUMENTS 4,256,834 3/1981 Zuk et al. ................................. 435/7
4,281,061 7/1981 Zuk et al. ................................. 435/7
4,284,412 8/1981 Hansen et al. ...................... 436/548

OTHER PUBLICATIONS

Nargessi et al., J. Immunolog. Methods, 26: 307–313, (1979).
Horan et al., Chemical Abstracts, 88:61022x, 275, (1978).

Primary Examiner—Esther M. Kepplinger
Attorney, Agent, or Firm—Bertram I. Rowland; Theodore J. Leitereg

[57] ABSTRACT

Improved results are achieved in fluorochromasia lymphocytotoxicity for cell typing by adding antifluorescer to reduce background fluorescence as a result of cell lysing.

3 Claims, No Drawings

4,532,203

FLUORESCENT DETERMINATION OF MICROLYMPHOCYTOTOXICITY

BACKGROUND OF THE INVENTION

1. Field of the Invention

In fluorochromosia lymphocytotoxicity, cells labelled with the vital dye carboxyfluorescein diacetate, which imparts a green fluorescence to living cells, but no fluorescence to dead cells, are reacted against cytotoxic monoclonal antibodies in tissue typing trays. The reaction can be assessed visually by an actual viability count of cells counterstained with ethidium bromide, which causes the dead cells to fluoresce with a red fluorescence. This manual method, while being very accurate, is also extremely time consuming.

Reactivity can also be determined by an automated system composed of a microscope mounted photomultiplier tube controlled by a computer, which detects residual green intracellular fluorescence in each well, as a quantative measure of cell viability. In preparing the trays for such automated readings, extracellular fluorescence from lysed cells must be removed by lengthy and complex steps of washing cells in the trays.

It is therefore desirable to find improved ways to simplify the technique which allows for automation, while maintaining the accuracy and efficiency of the automated system.

2. Description of the Prior Art

Bodmer et. al.: Application Of A Fluorochromatic Cyctotoxicity Assay To Human Leukocyte Typing. Histocompatibility Testing, 1967, page 231 describes use of carboxyfluorescein diacetate in tissue typing. Edidin, J. Immunol. (1970) 104:1303 describes counterstaining with ethidium bromide to determine dead cells in a manual method for counting. Bruning et. al., Tissue Antigens (1972) 2:473 describes an automated technique for determining cellular fluorescence.

SUMMARY OF THE INVENTION

An improved method for fluorochromasia lymphocytotoxicity is provided, where after labelling cells to be tested with a fluorescer, binding with specific antibody to the cell antigens and lysing specifically bound cells with complement, interference of fluorescent determination by extracellular fluorescer is removed by employing antifluorescer. The intracellular fluorescence is then determined.

DESCRIPTION OF THE SPECIFIC EMBODIMENTS

In accordance with the subject invention, a simplified method, particularly an automated method, for performing fluorochromasia lymphocytotoxicity is provided. Conventionally, the process involves isolating peripheral blood lymphocytes over Ficoll-Hypaque and labelling the lymphocytes with a vital dye fluorescer, one which is absorbed by the cells through the membrane, conveniently carboxy-fluorescein diacetate. The subject method does not require lymphocytes, nor does it require this particular fluorescer. However, since the fluorescer is conventionally used and provides satisfactory results, there is usually no need to use alternative fluorescers.

For cells that have been cryopreserved, after labelling the cells with the appropriate fluorescer, dead cells can be conveniently removed by relayering the labelled cell suspension over Ficoll-Hypaque. The resulting lymphocyte suspension is adjusted to the desired concentration in an appropriate nutrient medium. Conveniently, the cells will range from about $1-5 \times 10^6$ cells/ml.

The cellular suspension is dispensed into microtiter plate wells into which antibodies having the appropriate specificity for cell surface membrane antigens have been previously loaded. The mixture is then incubated for a sufficient time to provide for the binding to cells of homologous antibodies. After about a 0.5 hour incubation at ambient temperature, conveniently 22° C. is found to be satisfactory, a sufficient amount of complement e.g., rabbit complement, is added, and the mixture incubated again to ensure the lysis of all specifically bound cells. Usually, 1.5 hour at ambient temperature is found to be satisfactory.

At the completion of the incubation, receptor, usually antibody of fluorescer is added, which results in quenching of the fluorescer. A sufficient amount of the antifluorescer is added to ensure the complete binding of the fluorescer and, therefore, the substantially complete quenching of the extracellular fluorescer. Where the binding of the antibody does not result in complete quenching, various quenchers may be conjugated to the antibody to ensure the substantially complete absence of extracellular fluorescence. For example, 4,5-dimethoxyfluorescein can be conjugated to antibodies as a quencher for fluorescein to substantially completely quench the fluorescence of fluorescein when the 4,5-dimethoxyfluorescein conjugated antifluorescein binds to fluorescein. Upon addition of the antifluorescer, the trays may then be read for the presence of intracellular fluorescence. If the complement is not inactivated, the reading should be performed rapidly after the addition of the antifluorescer. However, the system can be stabilized by inactivating the complement by addition of EDTA or other convenient technique. In this way, non-specific lysing by the complement is minimized.

In the absence of the use of antifluorescer, extended washing is required involving a complicated series of steps, which can introduce errors into the measurement. Addition of a small amount of a non-ionic detergent e.g., Triton X-100, at about 0.5 to 1% in an appropriate aqueous buffered medium and storage at −20° C. helps stabilize the completed test preparation for later reading.

The following examples are offered by way of illustration and not by way of limitation.

EXPERIMENTAL

Materials and Methods

Anti HLA murine monoclonal antibodies in ascites are titrated (1λ well) in preoiled tissue typing trays. The antibody dilutions are in 3% bovine serum albumin (Miles Lab, Elkhart, IN) in Hanks balanced salt solution (Gibco, Grand Island, NY) and 0.2% sodium azide.

Two similar trays (I, II) of antibody titrations are prepared. Tray I is read on the automated system using the quenching antibody and is assessed by a visual cell viability count. Tray II is read on the automated system following the wash steps. A total of three different methodologies were involved; (1) visual; (2) automated with antifluorescer; and (3) automated without antifluorescer.

Preparation of Peripheral Blood Lymphocytes (PBLs)

Anticoagulated whole blood was obtained from normal volunteer donors. PBLs from these samples were isolated by Ficoll-Hypaque density gradient centrifugation and stored in liquid nitrogen until needed.

The frozen PBLs thawed for microlymphocytotoxicity are resuspended and washed in 20% fetal calf serum (FCS) in RPMI medium 1640 with Hepes buffer and L-Glutamine (Gibco, Grand Island, NY) before being labelled with carboxyfluorescein diacetate (Molecular Probes, Plano, TX) during a 15 minute incubation at 37° C. (Lizak, Human Immunol. (1980) 1:87). Relayering the labelled cell suspension over Ficoll-Hypaque removes the dead cells. One lambda of the lymphocyte suspension adjusted to a concentration of $2 \times 10^6$ cells/ml in 20% FCS in RPMI 1640 is dispensed per well to the antibody-preloaded trays. Following a 30 minute cell-antibody incubation at 22° C., 5λ of rabbit complement is added to each well. The complement incubation at 22° C. lasts 90 minutes.

Preparation of Tray I for Automated Reading with The Quenching Antibody and for Visual Cell Viability Count with Ethidium Bromide Following the 90 minute incubation, 1λ of sheep anti-fluorescein antibody diluted 1:2 in phosphate buffered saline is added per well to Tray I which is then immediately read on the automated system.

Two lambda/well of ethidium bromide (2,7 diamino-10-ethyl-9-phenyl-phenanthridinium bromide; Sigma Chemical Co., St. Louis, MO) is then added to Tray I for the visual cell viability percentage count which is done under low power fluorescence microscopy with appropriate filters for fluorescein excitation (Edidin, J. Immunol. (1970) 4:1303; Lizak, supra)

Preparation of Tray II for Automated Reading with Wash Steps

At the end of the complement incubation, Tray II is centrifuged (RT) for 3.5 minutes at $400 \times g$. The centrifuge is started slowly and only reaches the desired speed in 1.5 minutes. Complement and oil are blotted with a $2'' \times 3''$ absorbent bench cloth (S/P #L 5615-18) which is pressed onto the tray by a $2'' \times 3'' \times 1''$ foam rubber pad. The saturated cloth is stripped away with forceps. Using a 250λ dispense, each of the tray's 72 wells is washed 'hard drop' (prongs in wells before dispensing) with 10λ/well of 20% FCS in RPMI. Tray II is spun again (RT) for 3.5 minutes at $250 \times g$ with a very slow start. All supernatant is blotted as described previously. The wells are washed with 10λ/well of 20% FCS in RPMI 1640 'soft drop' (droplets are suspended from pron tips before insertion into wells). Tray II is spun a third time at RT for 3.5 minutes at $250 \times g$ with a slow start. This is followed by a last blotting of the tray.

Five lambda of a 0.7% solution of Triton X-100 in 0.01M Tris, pH 8.5, 56% (w/v) glycerol-water mixture is added to each well for the lysis of all remaining live cells. (Bruning, Tissue Antigens (1972) 2:473). Tray II is kept at $-20°$ C. for 20 minutes before it is read on the automated system.

Two murine monoclonal antibodies were tested. In a first comparison, the reactivity of W6/32 (a lymphocytotoxic $IgG_{2a}$ antiHLA-ABC antibody (Barnstable et. al. cell (1978) 14:9) against a random donor's PBLs is determined by the three different reading methods. In a second experiment A2,28M1, an IgM monoclonal antibody with anti-A2,A28 specificity (R=1.00) is tested against PBLs from HLA-A2+ and HLA-A2− donors, who were phenotypes according to routine procedures. (Lizak, supra) The following tables tally the percentages of viable PBLs as recorded by each reading method after lymphocytotoxic reaction with different dilutions of the two monoclonal antibodies.

TABLE I
Comparison of Viability of KCA PBLs at Different Dilutions of W6%/32 as Assessed by the Three Methods

| | QUENCHING | | | MEAN | WASH | | | MEAN | VISUAL | | | MEAN |
|---|---|---|---|---|---|---|---|---|---|---|---|---|
| W6/32 1:$10^4$ | 0 | 0 | 0 | 0 | 0 | 2 | 7 | 3.0 | 0 | 0 | 0 | 0 |
| 1:2 × $10^4$ | 0 | 0 | 0 | 0 | 4 | 1 | 0 | 1.7 | 0 | 0 | 0 | 0 |
| 1:5 × $10^4$ | 0 | 0 | 0 | 0 | 0 | 0 | 2 | .7 | 1 | 0 | 1 | .7 |
| 1:8 × $10^4$ | 10 | 10 | 11 | 10.3 | 15 | 8 | 19 | 14.0 | 10 | 12 | 8 | 10.0 |
| 1:$10^5$ | 4 | 26 | 32 | 20.7 | 21 | 28 | 27 | 25.3 | 22 | 26 | 24 | 24.0 |
| 1:2 × $10^5$ | 100 | 99 | 86 | 95.0 | 71 | 72 | 70 | 71.0 | 71 | 75 | 70 | 72.0 |
| 1:5 × $10^5$ | 100 | 100 | 100 | 100 | 86 | 71 | 94 | 83.7 | 76 | 80 | 79 | 78.3 |
| 1:8 × $10^5$ | 100 | 100 | 98 | 96.0 | 79 | 89 | 88 | 85.3 | 88 | 90 | 80 | 86.0 |
| 1:$10^6$ | 100 | 90 | 86 | 85.0 | 95 | 96 | 95 | 95.3 | 85 | 81 | 83 | 83.0 |
| 1:$10^7$ | 91 | 78 | 100 | 100 | 73 | 92 | 100 | 88.3 | 83 | 79 | 85 | 82.3 |
| 1:$10^8$ | 100 | 100 | 100 | 100 | 88 | 83 | 100 | 90.3 | 80 | 83 | 85 | 82.7 |
| 3% BSA | 100 | 100 | 91 | 97.0 | 98 | 95 | 100 | 97.7 | 100 | 89 | 95 | 94.7 |

TABLE II (1,2,3) Percentages of viable EE PBLs per well as determined by the three reading methods after microlymphocytotoxic reaction with A2,28M. The antibodies were dispersed in triplicate. The means are given.
(a) (+) control is W6/32 1:$10^4$; (−) control is 3% BSA in HBSS

| | (1) QUENCHING | | | a MEAN | (2) WASH | | | a MEAN | (3) VISUAL | | | a MEAN |
|---|---|---|---|---|---|---|---|---|---|---|---|---|
| W6/32 1:$10^4$ KM01 | 0 | 2 | 0 | .7 | 10 | 7 | 0 | 5.7 | 0 | 0 | 0 | 0 |
| 4B8H1C4 | | | | | | | | | 7 | 5 | 6 | 6.0 |
| 1:$10^2$ | 6 | 15 | 13 | 11.3 | 1 | 3 | 3 | 2.3 | 11 | 13 | 10 | 11.3 |
| 1:$10^3$ | 9 | 10 | 10 | 9.7 | 0 | 8 | 0 | 2.7 | 19 | 22 | 18 | 19.7 |
| 1:$10^4$ | 26 | 21 | 27 | 24.7 | 20 | 13 | 0 | 11.0 | 68 | 65 | 64 | 65.7 |
| 1:$10^6$ | 81 | 95 | 70 | 82.0 | 69 | 66 | 64 | 66.3 | 68 | 65 | 64 | 65.7 |

TABLE II-continued (1,2,3) Percentages of viable EE PBLs per well as determined by the three reading methods after microlymphocytotoxic reaction with A2,28M. The antibodies were dispersed in triplicate. The means are given.
(a) (+) control is W6/32 1:10⁴; (−) control is 3% BSA in HBSS

|  | (1) QUENCHING | | | a MEAN | (2) WASH | | | a MEAN | (3) VISUAL | | | a MEAN |
|---|---|---|---|---|---|---|---|---|---|---|---|---|
| $1:10^7$ | 86 | 77 | 100 | 87.7 | 86 | 98 | 78 | 87.3 | 63 | 70 | 65 | 66.0 |
| $1:10^8$ | 100 | 92 | 89 | 93.7 | 81 | 100 | 81 | 87.3 | 87 | 80 | 84 | 83.7 |
| $1:10^9$ | 100 | 100 | 95 | 98.3 | 93 | 93 | 93 | 93.0 | 85 | 80 | 85 | 83.3 |
| 3% BSA | 89 | 100 | 100 | 96.3 | 100 | 92 | 100 | 97.3 | 87 | 82 | 83 | 84.0 |

It is evident from the above results, that by using antibodies to the fluorescer, the process for determining the presence of cells having a specific surface membrane is greatly simplified. Rather than the extensive, complicated and cumbersome technique for removing the extracellular fluorescent molecules, the addition of antibodies to the fluorescer quenches the fluorescence, obviating the need to remove the extracellular fluorescent molecules. Thus, the automated system is substantially speeded up and simplified without loss of accuracy.

Although the foregoing invention has been described in some detail by way of illustration and example for purposes of clarity of understanding, it will be obvious that certain changes and modifications may be practiced within the scope of the appended claims.

What is claimed is:

1. In a method for detecting the presence of cells having a specific surface membrane antigen, said method comprising:

combining viable cells labelled with a vital fluorescent dye with antibodies for said surface membrane antigen and adding complement to lyse antibody bound labelled viable cells; and determining the presence of remaining labelled viable cells by their fluorescence in the substantial absence of extracellular fluorescence;

the improvement which comprises removing extracellular fluorescence by adding receptors to the fluorescer which quench the extracellular fluorescence.

2. A method according to claim 1, wherein said cells are peripheral blood lymphocytes.

3. A method according to any of claims 1 or 2, wherein said vital fluorescent dye is carboxy-fluorescein diacetate.

* * * * *